(12) United States Patent
Failor et al.

(10) Patent No.: US 7,069,608 B2
(45) Date of Patent: Jul. 4, 2006

(54) MULTI-PURPOSE PATIENT CHAIR

(75) Inventors: Raymond A. Failor, Seville, OH (US); Michael D. Fox, Rittman, OH (US)

(73) Assignee: TransMotion Medical, Inc., Sharon Center, OH (US)

( * ) Notice: Subject to any disclaimer, the term of this patent is extended or adjusted under 35 U.S.C. 154(b) by 0 days.

(21) Appl. No.: 10/750,442

(22) Filed: Dec. 31, 2003

(65) Prior Publication Data

US 2005/0138731 A1    Jun. 30, 2005

(51) Int. Cl.
*A61G 7/015* (2006.01)
*A61G 7/05* (2006.01)
*A61G 7/14* (2006.01)
*A61G 7/16* (2006.01)

(52) U.S. Cl. .............. 5/618; 5/601; 5/86.1; 280/650; 280/655.1; 297/423.35

(58) Field of Classification Search .............. 5/86.1, 5/618, 601; 280/647, 650, 655.1; 16/900, 16/438; 297/423.35
See application file for complete search history.

(56) References Cited

U.S. PATENT DOCUMENTS

| 3,147,039 | A | * | 9/1964 | Smith et al. ............. 297/90 |
| 3,534,432 | A | * | 10/1970 | Davies et al. ............. 16/437 |
| 4,632,450 | A | * | 12/1986 | Holdt ............. 297/84 |
| 5,042,487 | A | * | 8/1991 | Marquardt ............. 600/425 |
| 5,184,835 | A | * | 2/1993 | Huang ............. 280/47.371 |
| 6,341,406 | B1 | * | 1/2002 | Beckman ............. 16/113.1 |
| 6,616,174 | B1 | * | 9/2003 | Bierma ............. 280/655 |
| 6,912,746 | B1 | * | 7/2005 | Grove ............. 5/618 |

* cited by examiner

*Primary Examiner*—Alexander Grosz
(74) *Attorney, Agent, or Firm*—Renner, Kenner, Greive, Bobak, Taylor & Weber

(57) ABSTRACT

A medical chair provides a radiolucent backrest pivotally secured to a seat section. A pivoting push bar on the backrest pivots between an operative position, where it can be used to maneuver the chair, and a storage position where it does not compromise the radiolucent property of the backrest. The chair includes a leg support section, and the backrest and leg support section pivot between a chair structure and a stretcher structure. The pivoting of the backrest and legs support section are controlled by actuators that are positioned so as not to interfere with the radiolucent property of the backrest. A foot platform on the leg support section is connected to remain substantially parallel to the seat section as the leg support section is pivoted. A remote control allows for adjusting the configuration of the chair from points distant from the medical chair.

2 Claims, 10 Drawing Sheets

MULTI-PURPOSE PATIENT CHAIR

TECHNICAL FIELD

The present invention generally resides in the art of patient chairs and, more particularly, relates to a patient chair having features that make the chair particularly useful for radiographic and fluoroscopic procedures.

BACKGROUND ART

Mobile patient chairs are generally known in the art, and are used for patient transfer and transport, and, in some instances treatment and recovery, at medical facilities. They typically include a patient support structure that includes a seat section, a back rest, and a leg support section, wherein the back rest and leg support sections may be positioned relative to the seat section to provide a chair structure or stretcher structure, as needed. The support structure is generally carried on a base that rides on caster assemblies, which allow for transport of the patient chair. In these chairs, a patient can be quickly and safely moved from a sitting position to supine positions and vice versa.

Certain medical chairs in the prior art have been particularly useful in radiographic and fluoroscopic procedures wherein the patient is allowed to remain in the medical chair during such procedures. More particularly, some medical chairs are dimensioned to be received in radiographic and fluoroscopic machines (RF machines) at positions that allow a patient in the chair to be subjected to radiographic or fluoroscopic procedures. However, chairs in the prior art do not provide for manipulation of the support structure, particularly the back rest, once the medical chair is positioned in the RF machines. Thus, if it is determined that the patient is not properly oriented relative to the machine, or if the patient becomes uncomfortable, or, if for any other reason, the positioning of the support structure must be changed, the chair must be removed from its receipt in the RF machine.

Medical chairs used in conjunction with RF machines as generally disclosed above also typically include radiolucent back rests. With radiolucent back rests, radiographic or fluoroscopic procedures may be carried out to view medical conditions relating to the patient, from approximately the waist up to the top of the skull. However, the back rests of the prior art also typically provide push bars for transporting the medical chair on its caster assemblies. To preserve the radiolucent property of the back rest, these push bars are made to be removable from connection to the back rest. Because the push bar must be removed for a radiographic or fluoroscopic procedure, it presents a part that is separable from the remainder of the medical chair, and undesirably tedious to properly employ.

In some medical chairs, a foot rest portion may extend from the leg support section substantially perpendicular thereto to provide, as the name implies, a rest for the patient's feet. When the leg support section is raised to provide the medical chair with a stretcher structure, the foot rest must be folded down or else it will provide an obstruction to the patient when he or she attempts to lay down on the stretcher. In the prior art chairs, the foot rest must be manually manipulated to pivot upwardly against the leg support section in the stretcher structure, and must be manually manipulated to pivot downwardly in relation to the leg support section in the chair structure. This is another tedious and undesired exercise.

Thus there exists a need in the art for a medical chair that has a back rest that may be positioned even when the chair is placed within RF machinery. There also exists a need for a medical chair having a radiolucent back and a push bar for transporting the medical chair, wherein the push bar does not have to be removed to prevent obstruction of the radiolucent back. A need also exists for a medical chair having a foot rest portion that does not require constant tedious repositioning when the support structure of the chair is moved between a stretcher structure and a chair structure.

BRIEF DISCLOSURE OF THE INVENTION

In one embodiment, this invention provides a medical chair comprising a seat section; a radiolucent back rest pivotally secured to said seat section such that it may selectively extend from said seat section at desired positions in relation thereto; and a back rest actuator to selectively position said radiolucent back rest in relation to said seat section, wherein said back rest actuator does not compromise the radiolucent property of said radiolucent back rest. In medical chairs of the prior art, the mechanisms controlling the positioning of the back rest interfered to some degree with the radiolucent window of the back rests.

The prior art has also provided medical chairs having transport push bars that are removable to provide a radiolucent back rest, but the removal of the push bar is an added burden, and misplacing the push bar is common. Thus, in another embodiment, this invention provides a medical chair comprising a radiolucent back rest; and a push bar pivotally attached to said radiolucent back rest to move between an operative position, wherein said push bar is used to maneuver the medical chair, and a storage position, wherein said push bar does not compromise the radiolucent property of said radiolucent back rest.

The prior art has also failed to provide an efficiently functioning foot platform at the end of leg support sections. This invention provides such a medical chair comprising a seat section; a leg support section pivotally secured to said seat section such that it may selectively extend from said seat section at desired positions in relation thereto; and a leg support actuator that functions to adjust the position of said leg support section in relation to said seat section, wherein the position of said leg support section may range from substantially perpendicular to the plane of said seat section, in a chair configuration, to substantially parallel to the plane of said seat section, in a stretcher configuration; a foot rest section pivotally secured to said leg support section about an axis and providing a foot platform that remains substantially parallel to the plane of said seat section as said leg support actuator functions to adjust the position of said leg support section in relation to the plane of said seat section.

Each embodiment above, alone or in any combination, lends itself to an improved means for positioning a patient in radiographic and fluoroscopic machines (RF machines). More broadly, this invention provides a method for performing radiographic and fluoroscopic procedures on a patient, the method comprising the steps of supporting the patient in a medical chair comprising a seat section, a radiolucent back rest pivotally secured to said seat section such that it may selectively extend from said seat section at desired positions in relation thereto; and a remote control that controls the positioning of said radiolucent back rest relative to said seat section so that said radiolucent back rest is positionable from points distant from the medical chair; provisionally positioning the medical chair in a radiographic or fluoroscopic machine so as to provisionally position the patient supported thereon for a radiographic or fluoroscopic procedure; and adjusting the positioning of the medical chair and patient supported thereon with said remote control after said step of provisionally positioning the medical chair.

BRIEF DESCRIPTION OF THE DRAWINGS

For a complete understanding of the objects, techniques and structure of the invention reference should be made to the following detailed description and accompanying drawings wherein.

PREFERRED EMBODIMENT FOR CARRYING OUT THE INVENTION

Figure 1:
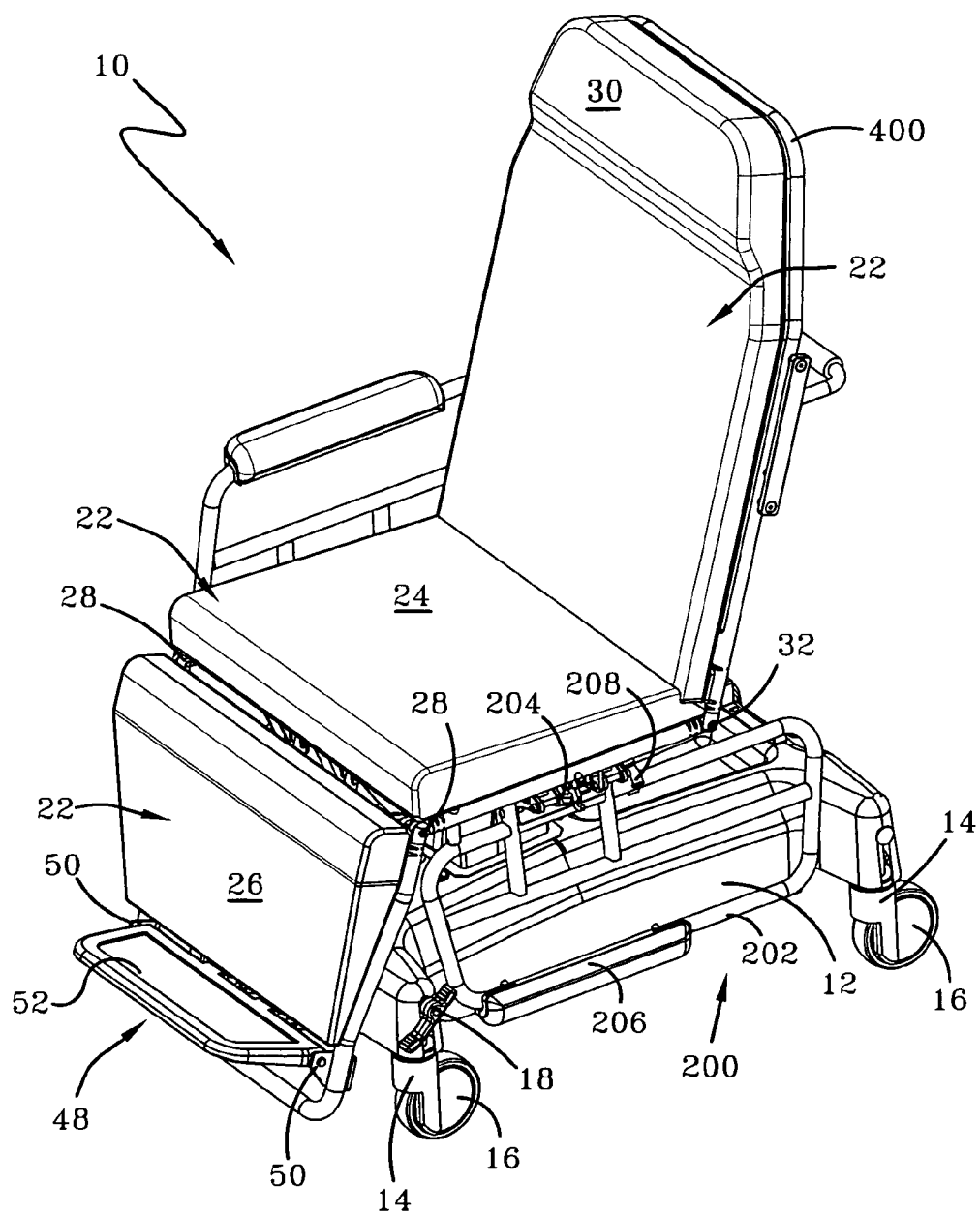
FIG. 1 is a perspective view of a medical chair in accordance with this invention.
Figure 2:
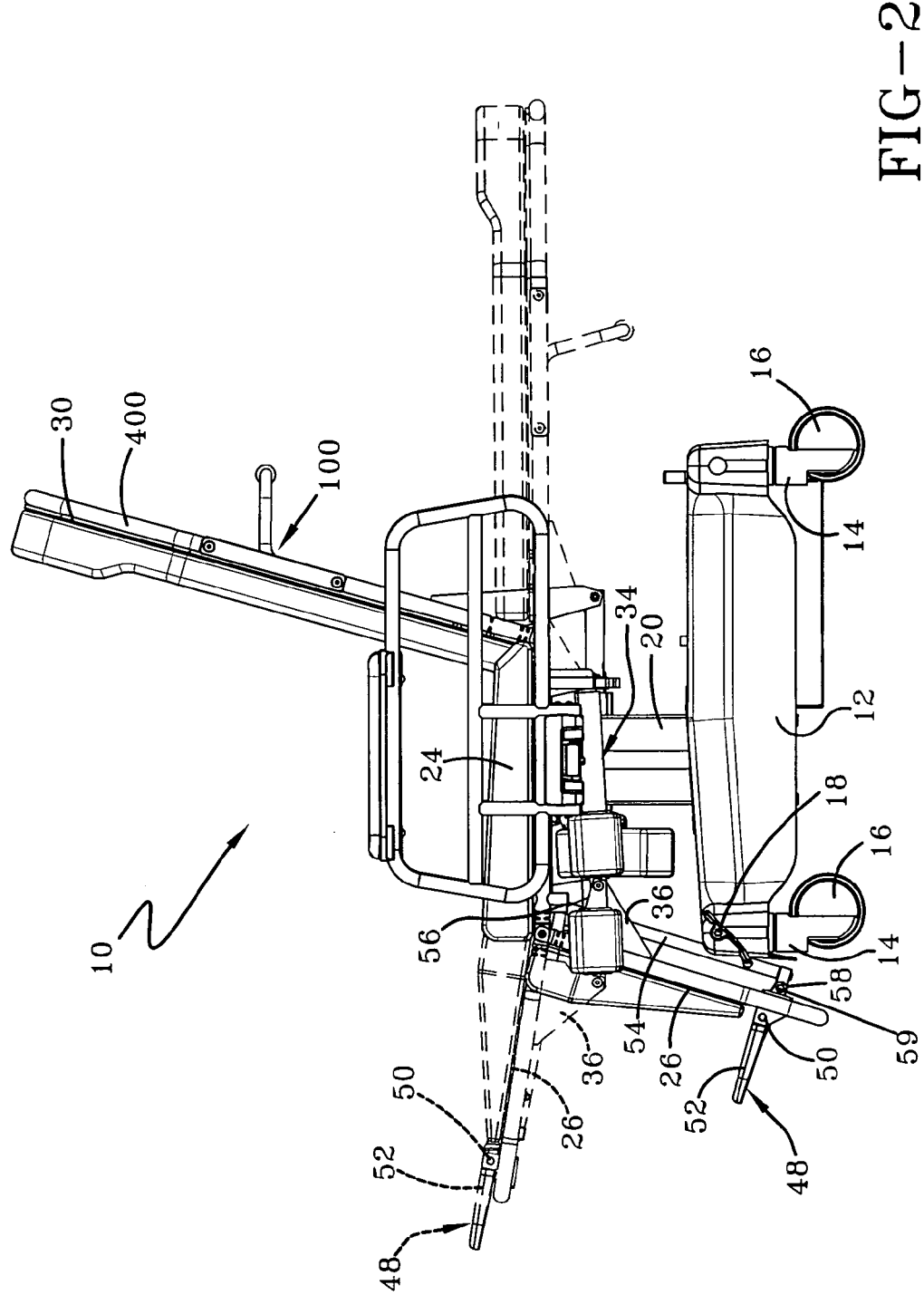
FIG. 2 is a side plan view showing the medical chair in a chair configuration and a stretcher configuration, the stretcher configuration being shown in phantom.

Referring now to FIGS. 1 and 2, a medical chair in accordance with this invention is designated generally by the numeral 10. Base 12 provides support for medical chair 10 and rides on a plurality of caster assemblies 14 and associated wheels 16 so that chair 10 is mobile. Central brake system 18 selectively controls the ability of the caster assemblies 14 to swivel and the ability of the wheels 16 to rotate and lock. Preferably, a four wheel brake and steer caster system is employed, such systems being generally known in the art.

Telescoping support column 20 extends upwardly from base 12 to support a patient support structure that is generally designated by the numeral 22. Patient support structure 22 includes various sections that may be positioned to provide a chair structure or stretcher structure or any compromise between these positions, as is generally known. Particularly, support column 20 supports seat section 24 generally parallel to the ground, and leg support section 26 is pivotally mounted to seat section 24 as at leg hinges 28. Similarly, back rest 30 is pivotally mounted to seat section 24 as at back hinges 32.

Figure 4:
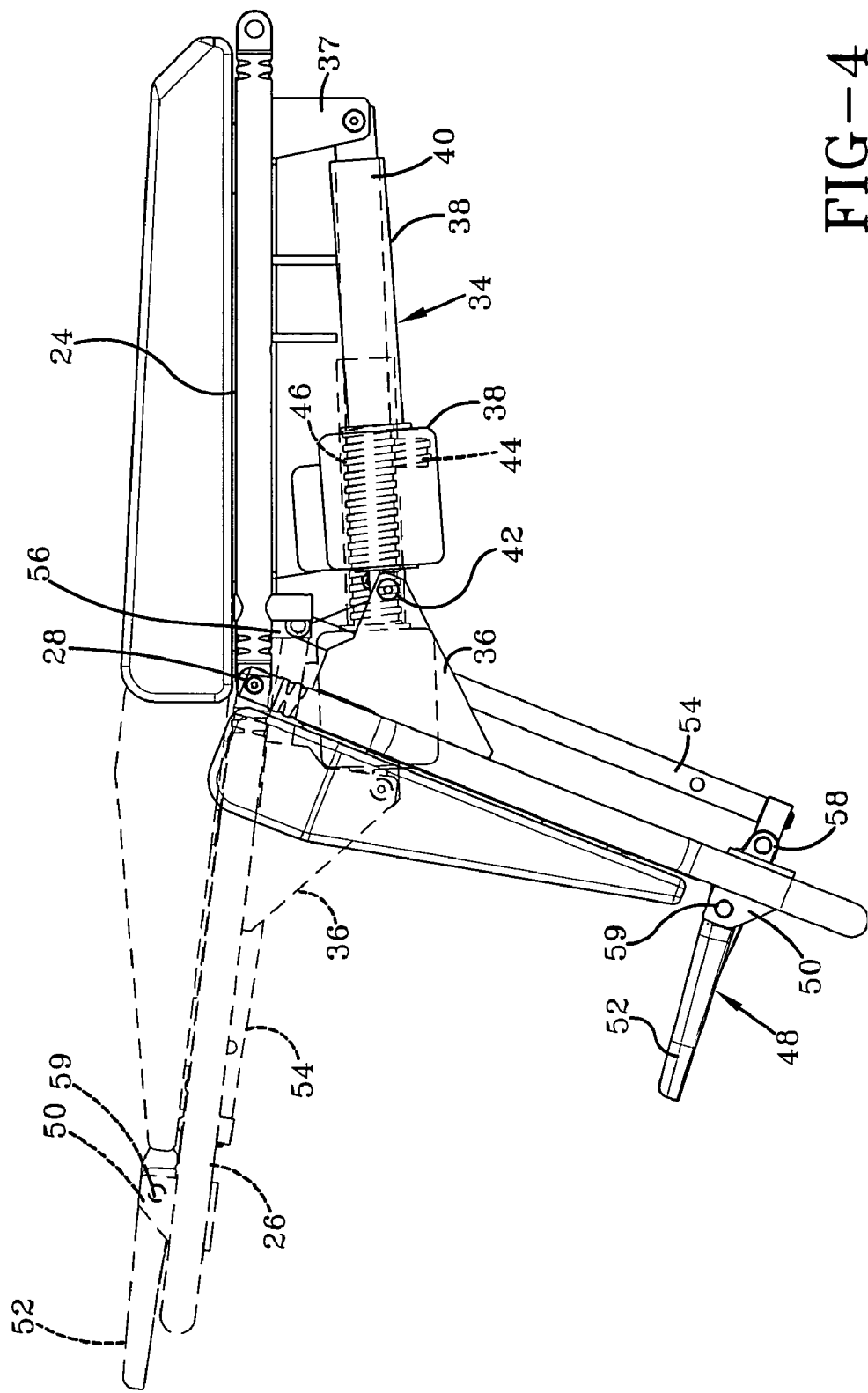
FIG. 4 is a detailed view of the general configuration of the actuators employed to alter the configuration of the medical chair.

Leg support actuator 34 is mounted to the underside of seat section 24, and communicates with leg support section 26 through mounting bracket 36. In FIG. 4, it is seen that sleeve 38, which pivotally attaches to bracket 36 at pivot pin 42, houses shaft 40, which pivotally attaches to mounting bracket 37 outside of sleeve 38. Sleeve 38 also houses a motor (not shown) that advances lead screw 44, which communicates with threaded portion 46 of shaft 40. By rotating lead screw 44 by means of the motor, sleeve 38 may be advanced to the left or to the right on shaft 40, thus regulating the angle at which leg support section 26 extends from seat section 24. At full retraction, leg support section 26 is substantially perpendicular to seat section 24 and, at full extension, is substantially parallel and on plane with seat section 24 (drawn in phantom in FIG. 2). It will be appreciated that medical chairs are sometimes constructed to provide true right angles between a seat section and a leg support section, and the term "substantially perpendicular" thus covers an actual perpendicular relationship, as well as those close to perpendicular. The same applies to "substantially parallel."

Although a specific physical structure has been defined for advancing leg support section 26, the functioning of leg support actuator 34 might be accomplished with other mechanisms, with the main concern here being the provision of an adjustable leg support section 26 at a position that does not interfere with the backrest of the chair. This will be disclosed more fully below.

Footrest 48 is pivotally secured to leg support section 26 at mounting brackets 50. Footrest 48 provides foot platform 52 substantially parallel to seat section 24. It is particularly preferred that foot platform 52 remain substantially parallel to seat section 24, even as leg support section 26 is moved from full retraction (i.e., in a chair structure positioning) to full extension (i.e., a stretcher structure positioning). Thus, at least one footrest link 54 is pivotally secured between seat section 24, at mounting bracket 56, and footrest bracket 58, which, it will be appreciated, is on the opposite side of the axis of rotation for footrest 48, as defined by the pivotal securement at pivot pins 59 in mounting brackets 50. As can be seen in FIG. 2, as leg support section 26 is raised to its full extension, foot platform 52 is maintained substantially parallel to seat section 24 during the raising of leg support section 26. This beneficial functioning of the foot platform might be accomplished with other mechanisms.

Backrest actuator 60 is also mounted to the underside of seat section 24, and pivotally communicates with mounting bracket 62 attached to backrest 30. Backrest actuator 60 operates through a sleeve, shaft, lead screw, and mounting bracket assembly, as does leg support section 26; however, at full extension, backrest 30 is substantially perpendicular to seat section 24 and, at full retraction, is substantially parallel and on plane with seat section 24 (FIG. 2).

Figure 3:
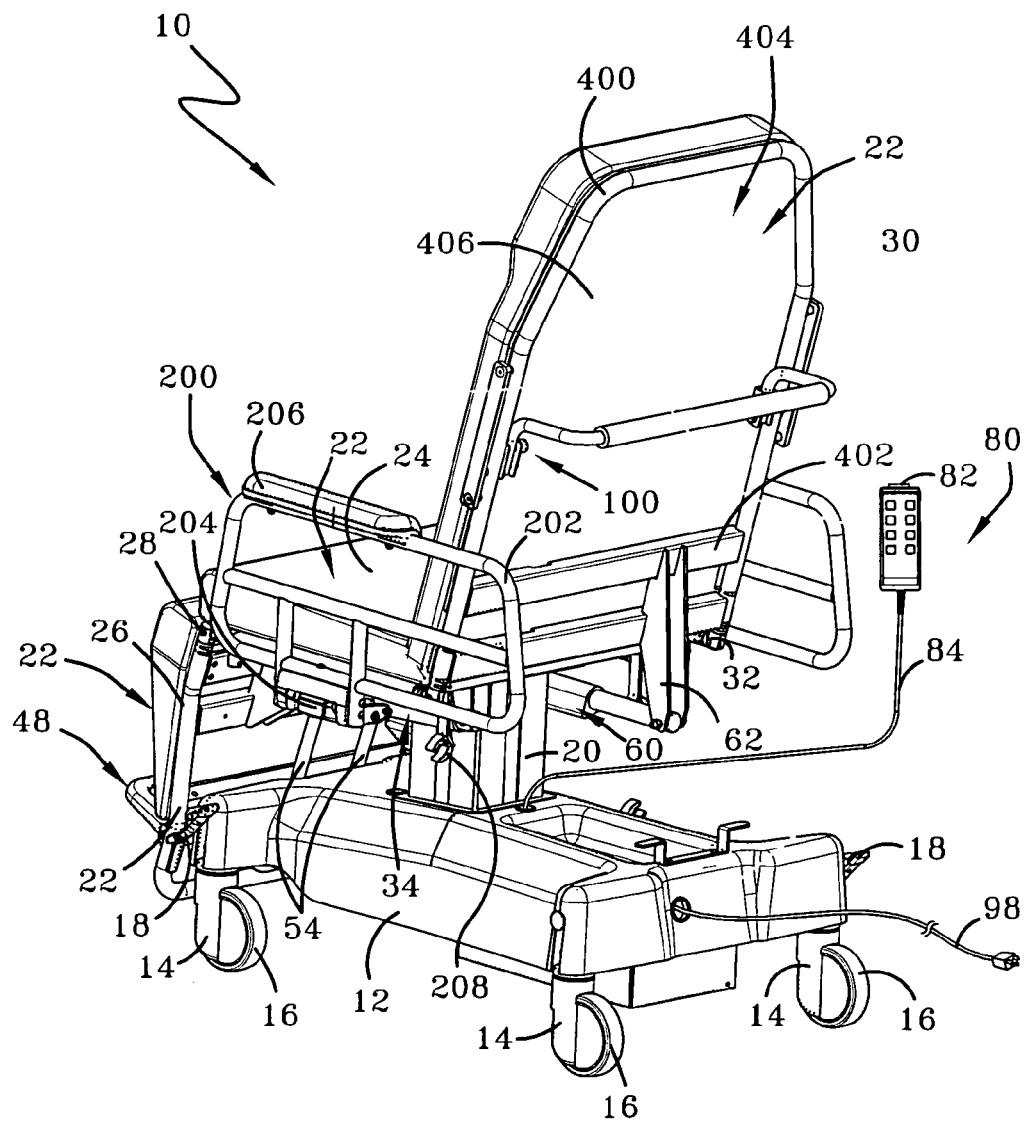
FIG. 3 is a rear perspective view of the medical chair.
Figure 5:
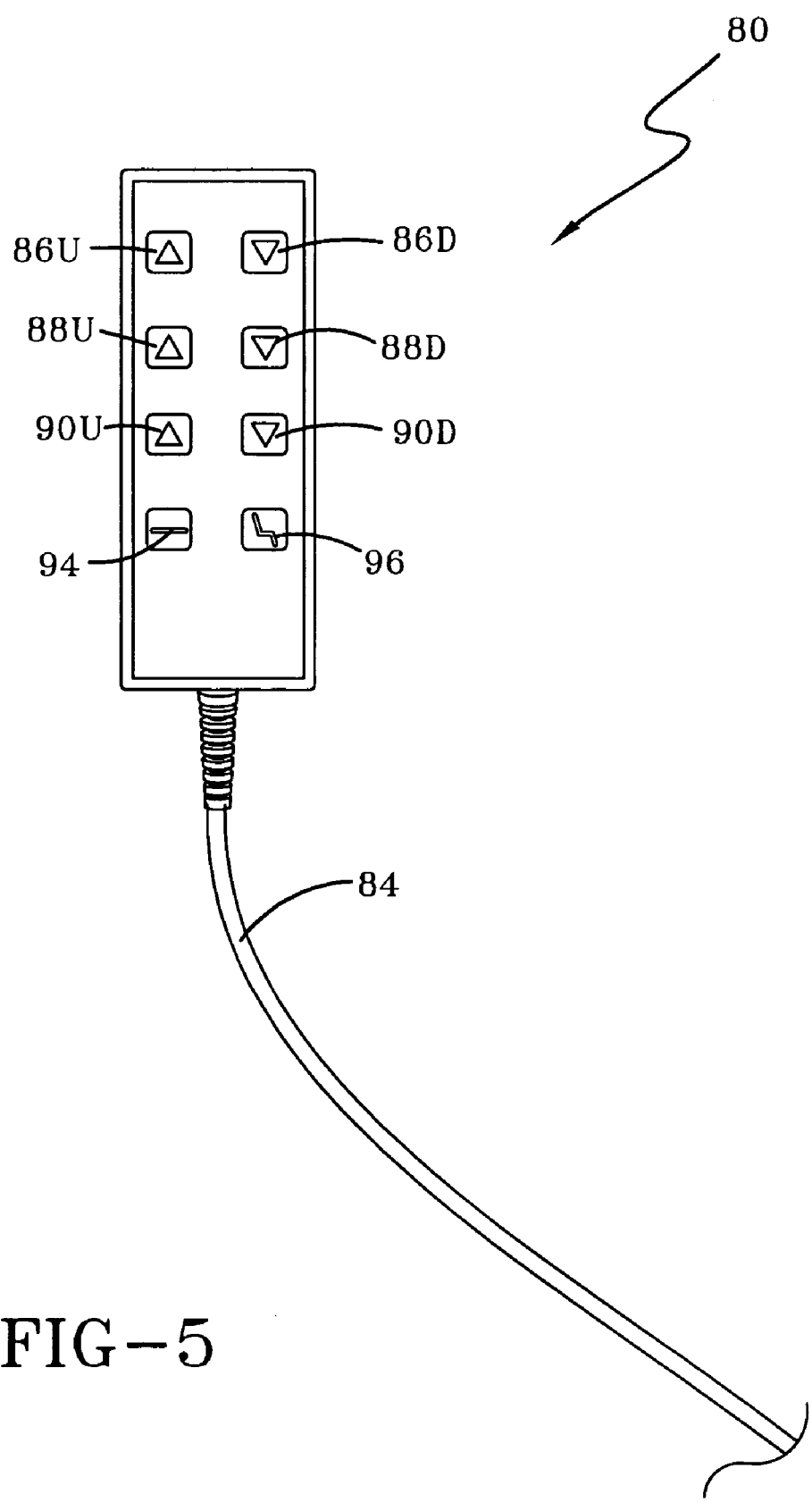
FIG. 5 is a closeup of the remote control that is used to alter the configuration of the medical chair.

Remote control 80 is provided to operate lead screw 44 of the leg support actuator 34 and the similar lead screw of backrest actuator 60, either individually or in tandem. Control 80 extends from connection with appropriate electronics in base 12 and, in addition to controlling lead screws, also controls the height at which telescoping support column 20 maintains seat section 24. With reference to FIGS. 3 and 5, control 80 includes control pad 82, electrically coupled by means of cord 84 to operate actuators 34 and 60 and adjust the height of telescoping column 20. Control pad 82 includes back adjustment up button 86U, and back adjustment down button 86D, which respectively serve to advance backrest 30 up towards the chair structure and down toward the stretcher structure. Similarly, control pad 82 includes leg adjustment up button 88U and leg adjustment down button 88D, which respectively serve to adjust leg support section 26 upward toward the stretcher structure and downward toward the chair structure. Telescoping support column 20 is adjusted by means of height adjustment up button 90U and height adjustment down button 90D. Finally, tandem stretcher button 94 serves to both raise leg support section 26 and lower backrest 30 so as to advance sections of patient support structure 22 toward the stretcher structure, and tandem chair button 96 serves to advance both leg support section 26 and back support section 30 toward their respective chair structure positions. Any appropriate electronics may be employed, and it is desired that control 80 be capable of being manipulated from a location remote from chair 10.

The power for electronic manipulation of the positioning of chair 10 may be supplied by battery or by common communication with a wall outlet, as indicted at cord 98. Preferably both means for supplying power are provided.

Figure 6:
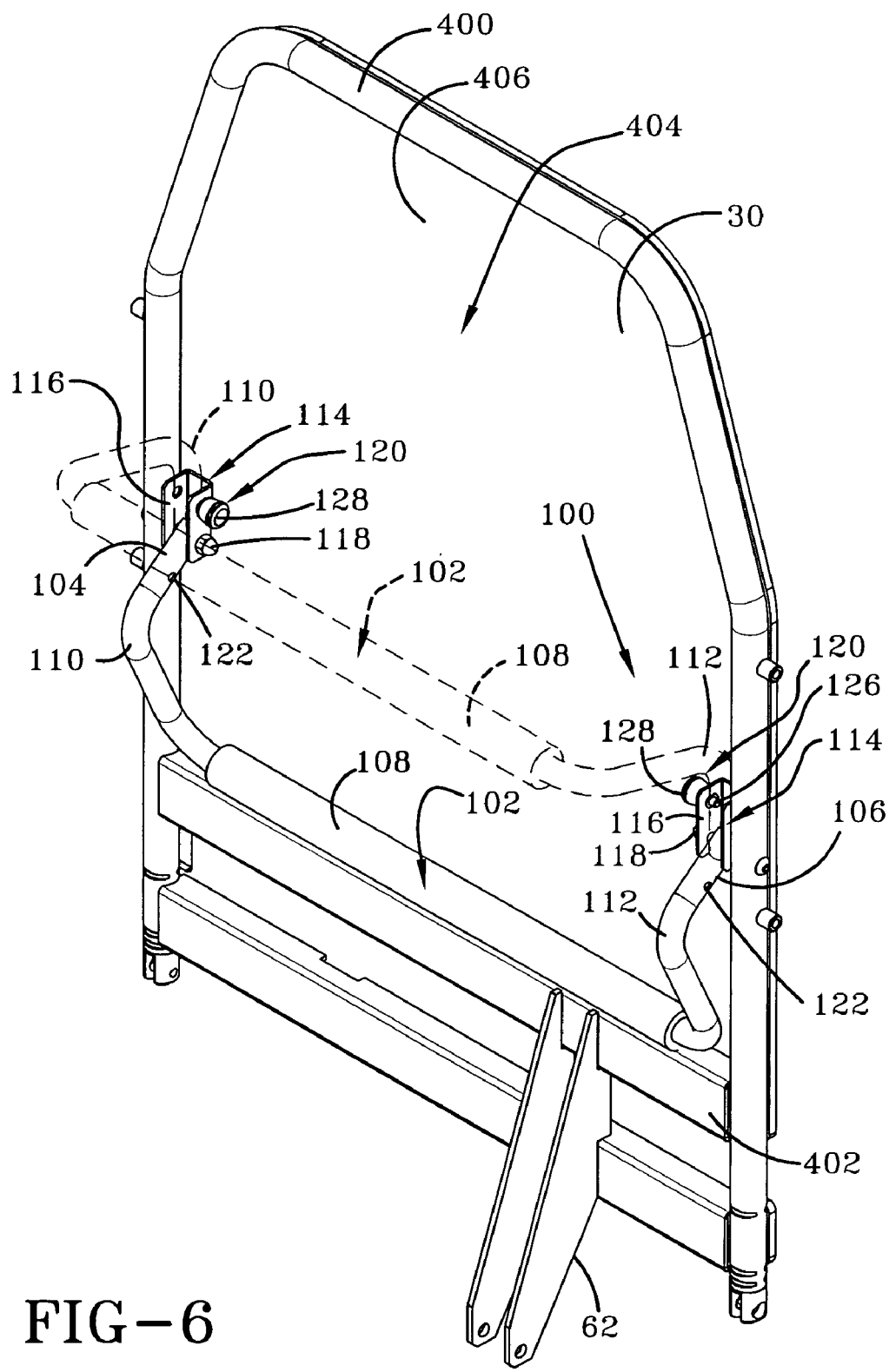
FIG. 6 is a perspective view of the backside of the backrest of the medical chair, showing the attachment of a push bar thereto, in an operative position (in phantom) and a storage position (non-phantom)

Referring now to FIGS. 3 and 6, it can be seen that push bar assembly 100 is provided on the back of backrest 30 to allow an attendant to maneuver chair 10. Push bar assembly 100 includes push bar 102 having first and second locking end portions 104, 106 that extend to grip portion 108 at bends 110, 112. First and second locking end portions 104, 106 are pivotally mounted to backrest 30 by associated locking mechanisms 114. Locking mechanisms 114 include mounting brackets 116, which pivotally secure first and second locking end portions 104, 106 as at pivot pins 118, so they can pivot between an operative position (in phantom in FIG. 6) and storage position (non-phantom).

In the operative position, locking plunger 120 extends into recesses 122 provided in end portions 104, 106, to lock push bar 100 in place. Locking plunger 120 is spring biased in a conventional manner to extend into recess 122 when push bar 102 is moved to its operative position, and plunger 120 is provided with beveled tip 126 to ramp over ends 104, 106 and "snap" into recess 122. Plunger grip 128 may be gripped and pulled to counter the bias on locking plunger 120 and remove it from engagement with recess 122, allowing push bar 102 to be pivoted to the storage position. The folding/storing position of the push bar is important in that it folds out of the way, thus permitting an unobstructed radiolucent clear backrest area, and, being attached at all times, it can not be lost or used as a weapon.

Preferred embodiments of medical chair 10 further include opposed side rail assemblies 200 that are pivotally mounted to seat section 24 to move from a support position, as shown in FIGS. 2 and 3, to a storage position, as shown in FIG. 1. Side rail assembly 200 includes rail weldment 202, affixed to rail hinge 204, which pivotally connects side rail assembly 200 to seat section 24 to pivot between a use position and a storage position. Arm pad 206 is secured to the top of rail weldment 202 to provide a comfortable armrest for a patient, in the use position. Clip 208, under seat section 24, clamps to a portion of rail weldment 202 to secure side rail assembly 200 in the storage position.

Figure 7:
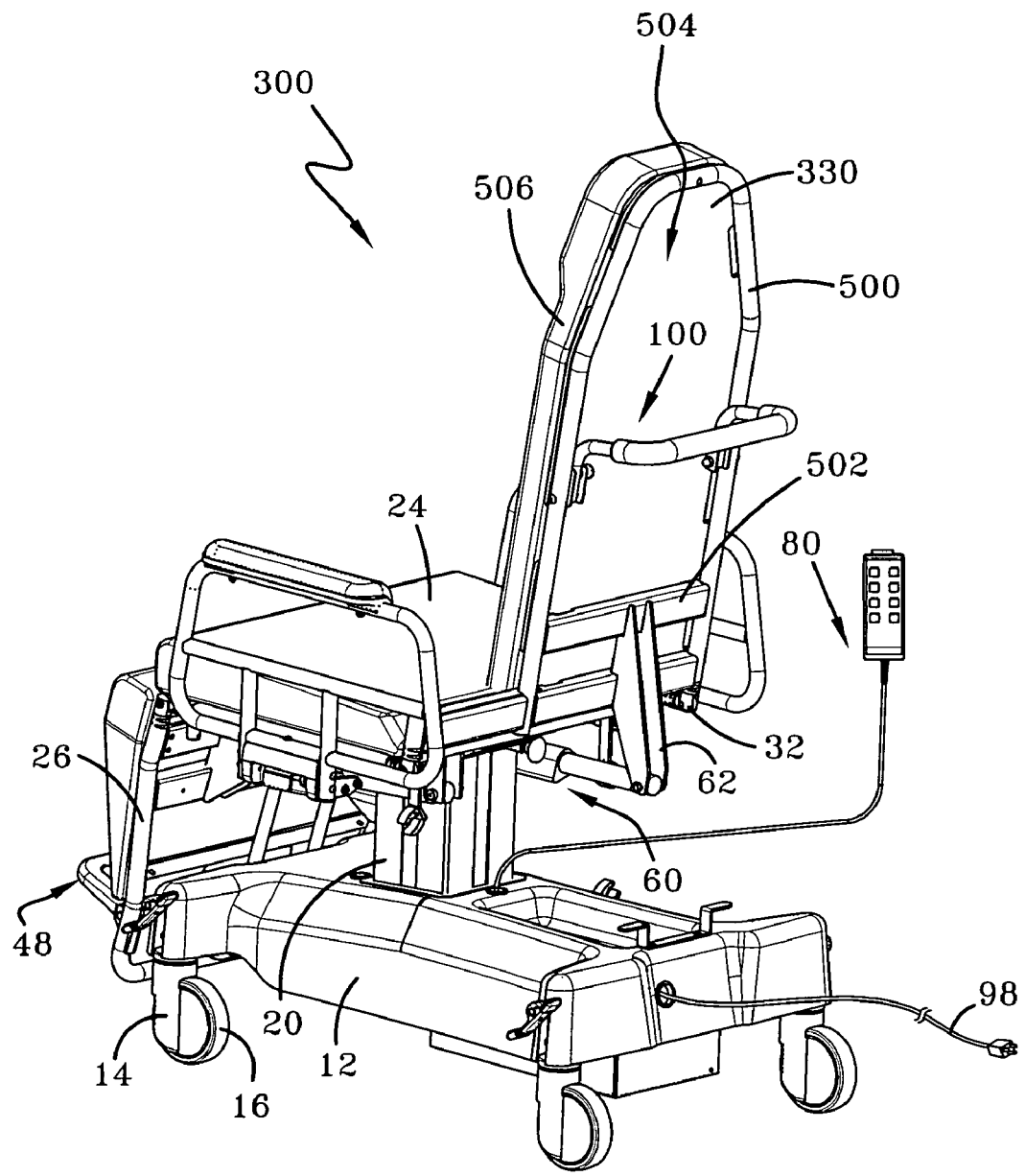
FIG. 7 is a perspective view of another embodiment of a medical chair, wherein the backrest portion of the chair is not sized as wide as the seat section of the chair, such that the medical chair shown therein is particularly useful in fluoroscopic procedures, as is generally known.

In the embodiments of FIGS. 1–3, seat section 24 and backrest 30 have substantially identical widths. In another embodiment of this invention, as shown in FIG. 7, an alternative medical chair 300 is shown having backrest 330. The focus here is on the alternative backrest 330, and other elements of chair 300 are substantially identical to chair 10 and have received like numerals to the extent necessary to disclose the particulars of backrest 330. Backrest 330 is pivotally mounted to seat section 24, as in the full-width backrest embodiment, at back hinges 32, and can be advanced toward a chair structure or stretcher structure by backrest actuator 60.

Backrests in accordance with this invention, whether full (as backrest 30) or narrow (as backrest 330), are preferably radiolucent. Thus, in particularly preferred embodiments, backrests 30, 330 are substantially defined by frame members 400, 500 and at least one bracket support 402, 502 that provide a window 404, 504 that is devoid of any material that would compromise the radiolucent property of the backrest. More particularly, radiographic backboards 406, 506 are provided in these respective embodiments, supported by frame members 400, 500. Radiographic backboards 406, 506 are formed from radiolucent materials, and may include, without limitation, phenolic materials, lexane materials and carbon fiber materials. It should be appreciated that, due to the existence of the at least one bracket support 402, 502, backrests 30, 300 may technically be described as not being 100 percent radiolucent. However, it is appreciated in the art that backrests of the type shown, like backrests 30 and 330, are "radiolucent" for all practical purposes inasmuch as the main torso area of a patient may be examined through radiographic or fluoroscopic procedures, even while the patient is resting in medical chair 10 or 300. In accordance with these embodiments, backrests may range in size, having widths of from about 12 inches to about 24 inches and heights from about 25 to 35 inches. Of this height, the bottom 6 to 8 inches might have its radiolucent property compromised by mounting bracket 62 and at least one bracket support 402, 502, but, again, such backrests are still considered to be radiolucent backrests.

Figure 8:
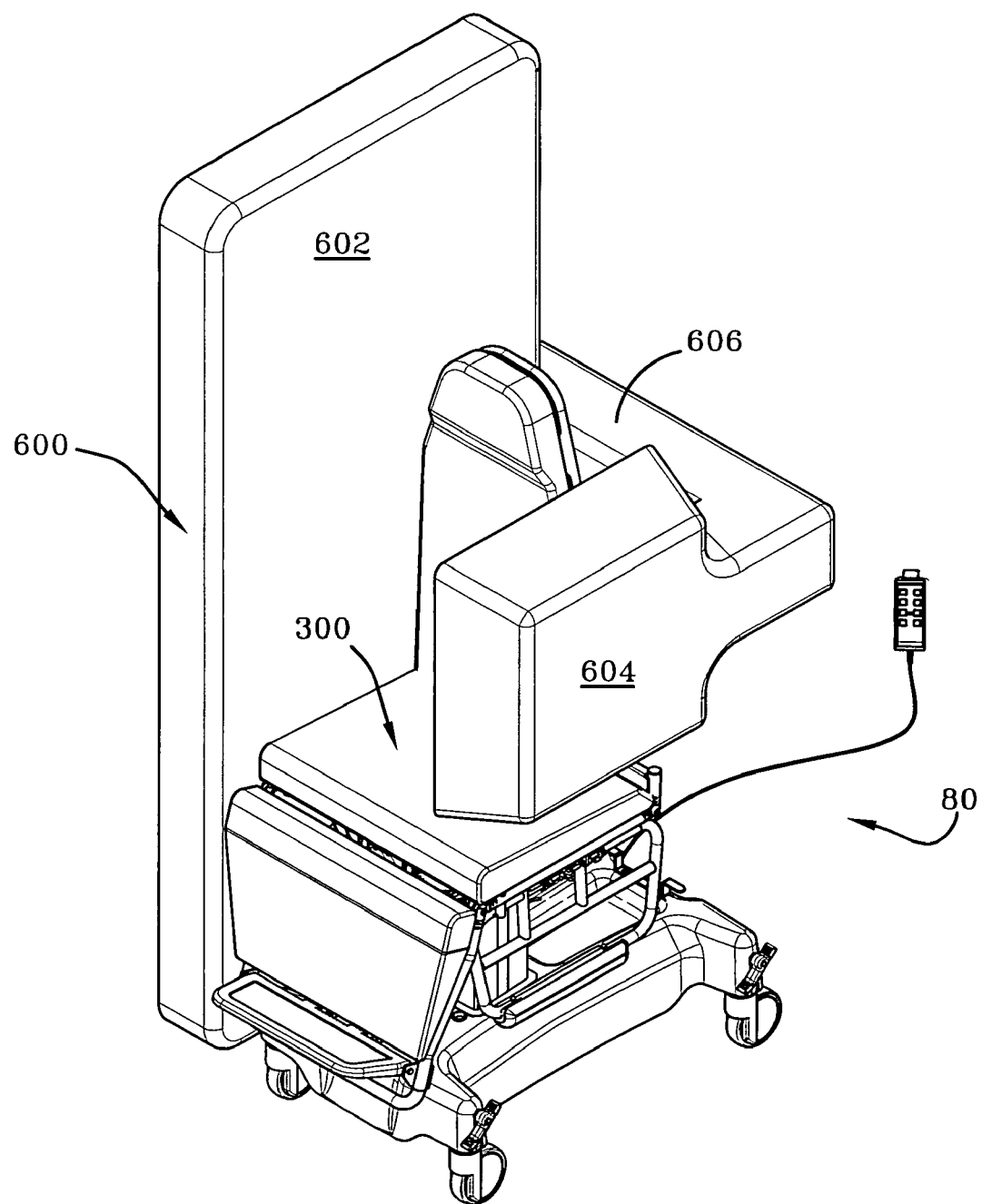
FIG. 8 is a perspective view of the use of the medical chair of FIG. 7 in a radiographic and fluoroscopic machine.

Referring now to FIG. 8, as is known, chairs shaped substantially as those shown here are desired for use in performing radiographic and fluoroscopic procedures on a patient. In FIG. 8, medical chair 300 is shown in a radiographic and fluoroscopic machine (RF machine) 600, positioned in the caliper opening between the table 602 and the image intensifier 604. Arm 606 connects between table 602 and image intensifier 604. In FIG. 8 backrest 330 is positioned substantially parallel to arm 606, although, as known in the art, medical chairs might be positioned in RF machine 600 with their backrest positioned perpendicularly to arm 606. In the latter case, it is particularly important that backrest be radiolucent, as there should be no obstruction between image intensifier 604 and table 602. In both situations, it might be necessary to further position the backrest or leg support section after provisionally positioning the medical chair between table 602 and image intensifier 604. Remote control 80 provides this beneficial ability to further position the chair from a position remote from RF machine 600. Intimate access to the medical chair, particularly the backside of the backrest is not required, as in the prior art.

Figure 9:
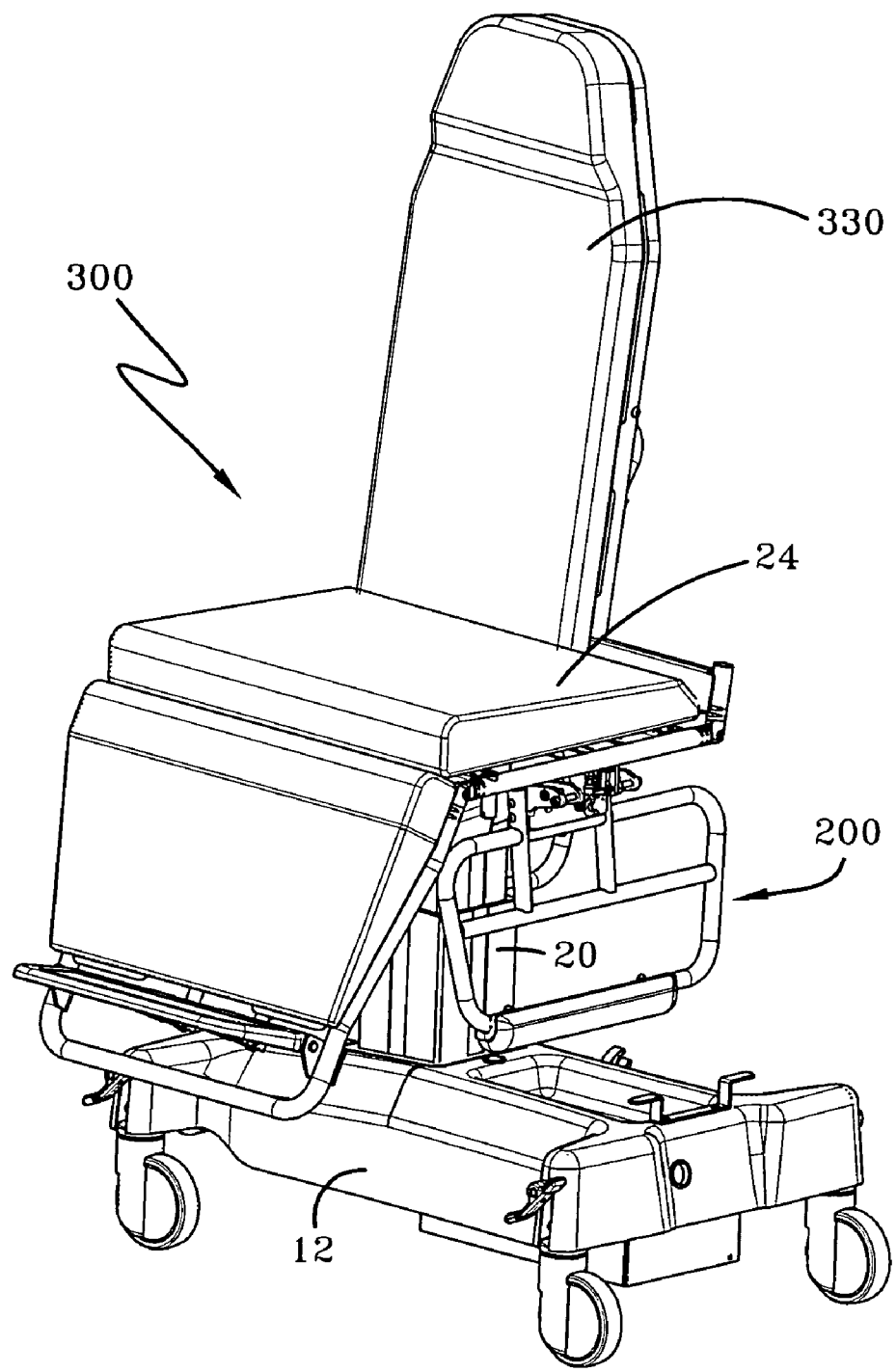
FIG. 9 is a perspective view of the medical chair of FIG. 7, shown with the patient support structure rotated on the telescoping support column 90 degrees relative to the base.
Figure 10:
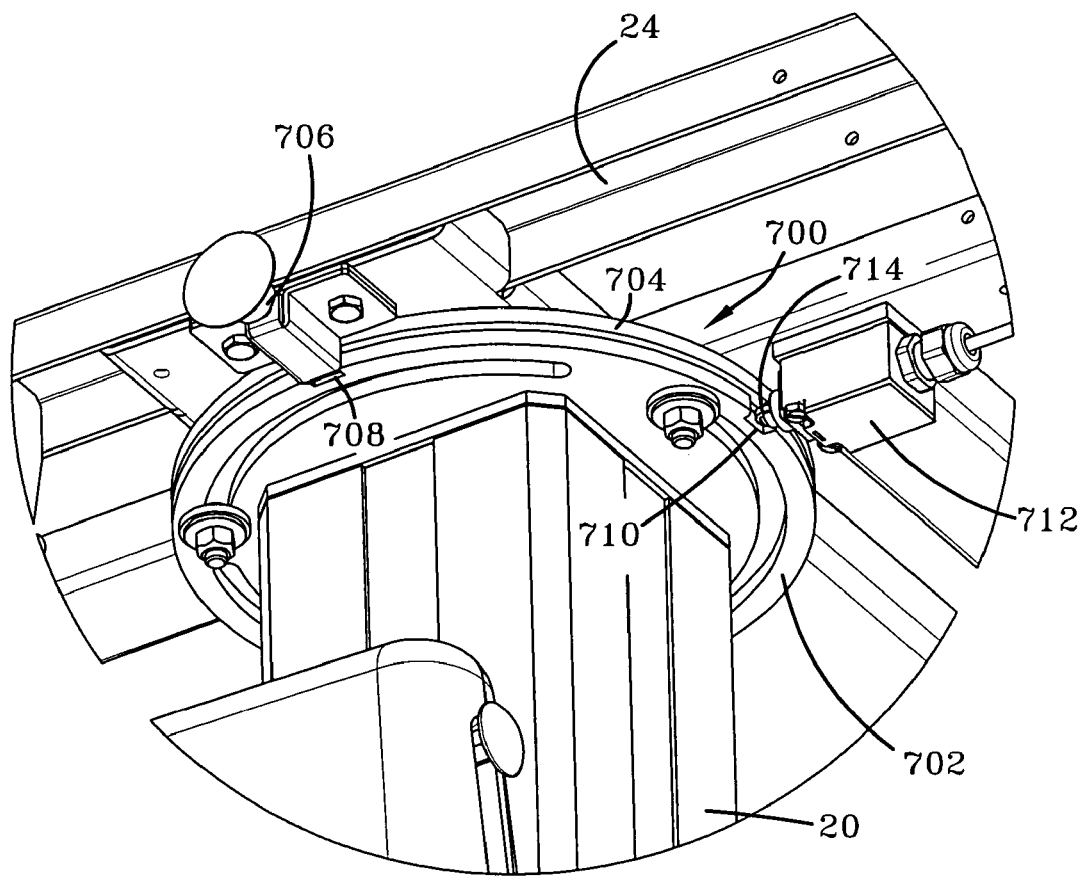
FIG. 10 is an exploded view of the underside of the seat section, showing connection between the seat section and the telescoping column.

To position a medical chair with its backrest perpendicular to arm 606, the seat section of the medical chair is fixed to the telescoping column so as to selectively pivot 90 degrees thereon. This is shown in FIGS. 9 and 10, with reference to medical chair 300. This position is provided only for use during specific RF procedures when the length of the base of the chair prevents the chair from fitting in the RF machine. In FIG. 9, seat section 24 has been rotated 90 degrees on telescoping column 20, as compared to the position of seat section 24 in FIGS. 7 and 8. In FIG. 10, seat section 24 is in the position shown in FIGS. 7 and 8, and the underside of seat section 24 and its interaction with telescoping column 20 is shown.

With reference to FIG. 10 it can be seen that the rotation of seat section 24 is accomplished by swivel assembly 700. Swivel assembly 700 includes a stationary disk 702, mounted on top of telescoping column 20, and a rotating disk 704 mounted to seat section 24. Rotating disk 704 and seat section 24 can thus rotate on stationary disk 702. Rotation is limited by the interaction of a plunger 706 with first and second notches 708 and 710, which are offset at 90 degrees along the 360 degree circle defined by disks 702, 704. By pulling on plunger 706 to remove it from notch 708, seat section 24 may be rotated until plunger 706 engages notch 710. When plunger 706 is engaged with notch 708, chair 300 is positioned as in FIGS. 7 and 8, and, when plunger 706 is engaged with notch 710, chair 300 is positioned as in FIG. 9.

In the position of FIGS. 7 and 8, it will be appreciated that side rails 20, whether up or down, extend outside of the boundaries of base 12, such that telescoping column 20 may be adjusted up or down in relation to base 12, without interference from side rails 200. In the position of FIG. 9, however, when side rails 200 are down, they rest directly above base 12, and lowering seat section 24 too far on telescoping column may cause side rails 200 to either crush base 12 or be crushed by thereby. Therefore, a cut-off switch 712 is provided offset 90 degrees from plunger 706 to engage notch 710 when plunger 706 engages notch 708, and serves to prevent the lowering of seat section 24 when positioned as in FIG. 9. Switch 712 includes a biased roller 714 that has an extended position, wherein it engages notch 710, as shown, and a retracted position, wherein biased roller 714 is pressed radially outward in relation to the center of stationary disk 702. The retracted position is reached when seat section 24 is rotated on stationary disk 702 such that biased roller 714 is pressed inward as it is forced out of notch 710. In the extended position, switch 712 is effectively off, and allows for the telescoping of seat section either up or down via telescoping column 20. In the retracted position, which is reached when seat section 24 is rotated to the position of FIG. 9, switch 712 is effectively on, and prevents the downward telescoping of seat section 24. Thus, when seat section 24 is positioned on telescoping column 20 in a position where side rails 200, if down, could be crushed by adjusting the height of seat section 24, switch 712 ensures that the downward adjustment means (e.g., height adjustment down button 90D of remote control 80) is switched off.

Thus, medical chairs of the type disclosed herein allow for improved radiographic and fluoroscopic methods. A patient may be first supported in the medical chair and provisionally positioned in the RE machine. Thereafter, the positioning of the medical chair may be adjusted to fine tune the positioning of the patient within the RE machine.

Thus it can be seen that the objects of the invention have been satisfied by the structure presented above. While in accordance with the patent statutes only the best mode and preferred embodiment of the invention has been presented and described in detail, the invention is not limited thereto by thereby. Accordingly, for an appreciation of the true scope and breadth of the invention reference should be made to the following claims.

The invention claimed is:

1. A mobile medical chair comprising:
   a seat section;
   a radiolucent back rest;
   a push bar pivotally attached to said radiolucent back rest to move between an operative position, wherein said push bar is used to maneuver the medical chair, and a storage position, wherein said push bar does not compromise the radiolucent property of said radiolucent back rest;
   a locking mechanism that selectively locks said push bar in its operative position, said push bar being pivotally attached to said radiolucent back rest by said locking mechanism;
   a leg support section, said leg support section and said radiolucent back rest being pivotally secured to said seat section such that they may selectively extend from said seat section at desired angles in relation to the plane of said seat section;
   a leg support actuator that functions to adjust the angle of extension of said leg support section in relation to the plane of said seat section, wherein the angle of extension may range from substantially perpendicular to the plane of said seat section in a chair configuration of the medical chair to substantially parallel to the plane of said seat section in a stretcher configuration of the medical chair; and
   a back rest actuator that functions to adjust the angle of extension of said radiolucent back rest in relation to the plane of said seat section, wherein the angle of extension of said radiolucent back rest may range from substantially perpendicular to the plane of said seat section in said chair configuration to substantially parallel to the plane of said seat section in said stretcher configuration, and wherein said leg support actuator and said back rest actuator are located beneath said seat section and do not compromise the radiolucent property of said radiolucent back rest.

2. The medical chair of claim 1, wherein said push bar, in said storage position, does not obstruct the proper positioning of said medical chair in radiographic and fluoroscopic machines.

* * * * *